United States Patent [19]

Liu et al.

[11] Patent Number: 5,149,368

[45] Date of Patent: Sep. 22, 1992

[54] RESORBABLE BIOACTIVE CALCIUM PHOSPHATE CEMENT

[76] Inventors: Sung-Tsuen Liu, 29 Landing, Laguna Niguel, Calif. 92677; Harvey H. Chung, 43 Via Costa Verde, Rancho Palos Verdes, Calif. 90274

[21] Appl. No.: 639,536

[22] Filed: Jan. 10, 1991

[51] Int. Cl.$^5$ ............................................... C09K 3/00
[52] U.S. Cl. ..................................... 424/602; 106/35; 501/1
[58] Field of Search ................. 501/1; 623/16; 106/35; 433/228.1

[56] References Cited

U.S. PATENT DOCUMENTS 4,668,295 5/1987 Bajpai ................................... 106/85

*Primary Examiner*—Karl Group
*Assistant Examiner*—Chris Gallo
*Attorney, Agent, or Firm*—Drucker & Sommers

[57] ABSTRACT

This invention provides a calcium phosphate cement with relatively high surface pH which is very beneficial from the biocompatibility point of view. When calcium phosphate salts react with an acidic reagent to form cement, it normally involves the dissolution and recrystallization process. The acidity of the setting cements depends strongly on the nature of the calcium phosphate salt used, the acidity of the setting reagent, and the reaction rate. The present invention uses high alkaline calcium phosphate ceramics such as tetracalcium phosphate alone or together with calcium phosphate ceramics such as α-tricalcium phosphate as base cementing powder to increase the surface pH of the setting cement.

14 Claims, No Drawings

RESORBABLE BIOACTIVE CALCIUM PHOSPHATE CEMENT

BACKGROUND OF THE INVENTION

1. FIELD OF THE INVENTION

This invention relates to bioresorbable cement setting reagents particularly to those formed from calcium phosphates, and useful in dental and bone cements, bone graft materials, bone substitutes, bone fillers, as a drug release carrier, and in other medical applications.

2. DESCRIPTION OF THE PRIOR ART

The major inorganic constituent of hard tissue is biological apatite. For example, bone has 65% to near 70% of biological apatite, and teeth contain more than 98% biological apatite. Hydroxyapatite is a calcium phosphate compound which has same crystal structure as biological apatite. In principle, hydroxyapatite should be an ideal candidate as hard tissue replacement material. However, the precipitated hydroxyapatite has very fine particle size. Because of manipulation requirements, this hinders the applications of precipitated hydroxyapatite in the medical area. In the last twenty years or so, many types of calcium phosphate ceramics have been prepared. Among these, hydroxyapatite and 62-tricalcium phosphate ceramics and calcium phosphate containing glass have been extensively studied. Clinical studies confirmed that most of the calcium phosphate ceramics such as hydroxyapatite, tricalcium phosphate, tetracalcium phosphate and dicalcium phosphate have excellent biocompatibility and can be well accepted by both hard tissue and soft tissue. The experimental results also indicated that dense hydroxyapatite is non-bioresorbable while other porous calcium phosphate ceramics are bioresorbable.

Calcium phosphate ceramics have been approved as useful and biocompatible materials for bone substitutes. These include dicalcium phosphate, tricalcium phosphate, apatite compounds and tetracalcium phosphate. Most of the calcium phosphate ceramics for medical application are prepared either as granule form or block form. The granule form has a mobility problem while the block form is very brittle and is difficult to shape. In order to solve the above problems, many attempts have been made to prepare bioresorbable grouts or cementing materials. Among these are Plaster of Paris, collagen and several types of calcium phosphate cement.

Ideally, a useful cementing material for hard tissue application should have good biocompatibility, suitable bioresorption rate, and good setting character with reasonable setting time. Most of the above materials have certain disadvantages. Plaster of Paris have reasonable setting character but the resorption rate is too fast. Collagen-hydroxyapatite composite and polylactate-HA composite can serve as useful delivery system for hydroxyapatite granule. However, these materials can only be made as premolded shape and cannot be molded at the surgical site. Polyacrylic acid calcium phosphate cement is not bioresorbable and the setting cement is too acidic.

Recently, a calcium phosphate cement with bi-functional organic acids or amino acids has been reported (U.S. Pat. No. 4,668,295). However, this cement is also very acidic and disintegrates very fast in the liquid environment. It has been noted that in practice such a cement gives a low pH product which can be irritating and not well tolerated. No ingredients that would raise the pH closer to neutral are disclosed therein.

Pure hydroxyapatite cement prepared by reacting tetracalcium phosphate and other calcium phosphate is not resorbable and does not have good setting character (U.S. Pat. Nos. 4,518,430 and 4,612,053). An octacalcium phosphate cement prepared by reacting hydroxyapatite and dicalcium phosphate has also been reported Oonishi[1] studied the α-tricalcium phosphate bioactive cement using citric acid as setting reagent. The cement has reasonable setting time and strong mechanical strength However, the cement is very acidic in nature. More, recently a calcium phosphate containing bioglass cement using phosphoric acid or calcium hydroxide as setting reagent has been reported by E. A. Monroe[2] and his co-workers.

[1] "Studies on Development of α-TCP Bioactive Bone Cement" H. Oonishi, et al, Osaka-Minami National Hospital.
[2] Abstract Phosphate Glass Bone Graft. Published at the 15th Annual Meeting of the Society for Biomaterials April 28, May 2, 1989 Lake Buena Vista, Fla., U.S.A.

The development of moldable bioresorbable calcium phosphate cement would expand the medical application of calcium phosphate ceramics considerably.

Most of the previous calcium phosphate cements developed used hydroxyapatite and tricalcium phosphate as cementing powder, and used acids such as phosphoric acid, bi-functional organic acids, citric acid or polyacrylic acid. These cements are normally very acidic in nature and take a very long time for them to reach neutral pH. After implantation, these cements would cause irritation and inflammatory reaction. Beside, these cements are difficult to control the setting time and do not have good manipulation characteristics.

SUMMARY OF THE INVENTION

This invention provides a calcium phosphate cement with relatively high surface pH which is very beneficial from the biocompatibility point of view. When calcium phosphate salts react with an acidic reagent to form cement, it normally involves the dissolution and recrystallization process. The acidity of the setting cements depends strongly on the nature of the calcium phosphate salt used, the acidity of the settling reagent, and the reaction rate. The present invention uses a high alkaline calcium phosphate ceramic such as tetracalcium phosphate alone or together with a calcium phosphate ceramic such as α-tricalcium phosphate as the base cementing powder to increase the surface pH of the setting cement.

The present invention seeks to provide bioresorbable calcium phosphate cements which can be used as hard tissue replacement materials. These cements can be moldable at the surgical site with reasonable setting time or can be prepared as premolded shapes. The basic constituent of the cement is the strongly alkaline tetracalcium phosphate, and the setting reagents are citric acid or the combination of acidic citrate compounds with other soluble biocompatible salts. To control the bioresorption rate, a variety of biocompatible compounds can be added as filler for these cements.

These cements are only slightly acidic during the beginning of setting. After setting, the surface pH of the cements raises rapidly to near 7 or higher in a rather short period in the liquid environment. During dissolution, the cements form only constituents or ions which are also the compositions of the body fluid. Advantages of these cements are relative high surface pH, good biocompatibility, bioresorbability, reasonable setting time and good manipulation character. These cements would be very useful as implants for hard tissue replacement materials. They can be used for bone grafts, bone defect fillers, dental cements and bone cements. They can also be used as binder system for granule hydroxyapatite and as a drug delivery system.

As aspect of this invention is a cementitious paste for orthopaedic and dental applications comprising:

a cementing powder selected from the group consisting of tetracalcium phosphate;

a setting reagent selected from a group consisting of citric acid, $NaH_2$ citrate, and $Na_2H$ citrate, wherein the Weight ratio of cementing powder to setting reagent ranges from 2:1 to 15:1; and sufficient water to form a paste, and which paste, after setting, has a pH greater than 5.

DESCRIPTION OF THE PREFERRED EMBODIMENTS

Among the calcium phosphate salts, the monocalcium phosphate is acidic while the aqueous suspensions of dicalcium phosphate, tricalcium phosphate or hydroxyapatite show near neutral pH. The only calcium phosphate ceramic which shows strong alkaline character is tetracalcium phosphate. By using this ceramic as cement powder, it can release hydroxide ion to neutralize the acidic setting reagent immediately. Even after setting, the excess unreacted powder can still leach hydroxide ion resulting in a rapid increase of the surface pH to near neutral or higher.

By reacting the calcium phosphate salt, having a Ca/P mole ratio equal to 1.5 or higher, with polyfunctional organic acids, the calcium phosphate salt will dissolve and form dicalcium phosphate and the corresponding calcium organic salts during the setting stage. The extent of the reaction, the setting time and the setting character are sensitive to the nature of cement powder, the pH and the type of setting reagent. For example, the dissolution rate of calcium phosphate salts having a mole ratio of 1.5 or higher of Ca/P follows the order; tetracalcium phosphate > $\alpha$-tricalcium phosphate > $\beta$-tricalcium phosphate > hydroxyapatite. By using citric acid as the setting reagent, both tetracalcium phosphate and $\alpha$-tricalcium phosphate can form good setting cements in a rather short time. In contrast, both hydroxyapatite and $\beta$-tricalcium phosphate, because of their slow dissolution rate, cannot form a good setting cement with citric acid.

A further increase of the surface pH of the setting cement is made by using hydrogen citrate salt or citric acid with alkaline reagents instead of using pure citric acid as setting reagent. Among the suitable hydrogen citrate salts used are sodium dihydrogen citrate, ammonium dihydrogen citrate or potassium dihydrogen citrate. Also useful as pH modifiers are NaOH, KOH, $NH_4OH$, Sodium citrate potassium citrate, ammonium citrate, sodium phosphate, disodium hydrogen phosphate, potassium phosphate, and dipotassium hydrogen phosphate. If the combination of citric acid and alkaline reagents is used, the combined reagents solution can be adjusted to have pH values ranging from approximately 3 to 5. The pH of a concentrated pure citric acid stays normally near 2. In contrast, the above setting reagent should provide an initial solution pH which is much higher than the pure citric acid. After setting, surface pH of the setting cement will stay near 5 and raises to near neutral or higher in a rather short period.

Another concern of the implantable cement as hard tissue replacement material is the bioresorption rate of the cement. A single component cement system such as Plaster of Paris would lack the flexibility in controlling the bioresorption rate. When the setting Plaster of Paris is implanted, it resorbs too fast to match the bone growth. In the present cementing system, the weight ratio of calcium phosphate cementing powder to the setting reagent stays at least 2 or higher. The ratio can raise to as high as 15. Therefore, the final setting cement contains the reaction products and considerable amount of un-reacted calcium phosphate. Both reaction products and the un-reacted calcium phosphate ceramics such as tetracalcium phosphate and tricalcium phosphate are bioresorbable.

In order to meet specific need for controlling the bioresorption rate, a biocompatible material in the form of fine powder or granule, having particle size ranging from 1 micron to 20 mesh, is used as filler for the cementing system. Beside having a good biocompatibility, the filler should not show significant effect on the integrity and setting behavior of the cement. These useful fillers include tricalcium phosphate, calcium phosphate apatite, dicalcium phosphate, calcium carbonate, calcium sulfate dihydrate, calcium sulfate hemihydrate, calcium sulfate anhydrous, calcium fluoride, calcium oxide, calcium citrate, magnesium hydroxide, magnesium oxide and other sparingly soluble calcium organic salts.

In the present invention of calcium phosphate cements, the cementing powder was premixed with filler material to form a homogeneous mixed powder. The setting chemicals can be prepared by two methods: 1) dissolving the setting reagent in water or saline water to form an aqueous setting solution; or 2) premixing the solid setting reagents with the cementing powder, and using sterilized pure water or saline water as the setting aqueous solution.

The cements of present invention may be used as bioresorbable cement or cements for: 1) bone grafts, bone defect filler or replacement of bone that has been removed surgically or due to trauma; 2) material for ridge augmentations; 3) jaw repairs; 4) cranial and maxillofacial surgeries; 5) luting cement in dentistry and orthopaedic surgery; 6) spinal fusions; 7) endodontic filling material; 8) root cement; 9) replacing or promoting regeneration of bone mineral lost due to periodontal disease; and 10) drug release systems. Antibiotics are the preferred drugs to be released by the cement of this invention.

The strength as well as the setting time of the present cements depends strongly on the nature and particle size of the calcium phosphate and the filler powder, the type and amount of the setting reagent, and the solid powder to liquid ratio. In general, by keeping other factors the same, the strength normally increases by reducing the particle size of the powder. The setting time increases with decreasing the cement powder to setting reagent ratio.

The cement can be pre-set to any shape before use. For example, in the use as a drug delivery system, the required amount of the drug is mixed with the cementing powder and setting reagent to form paste first. After set time, the hardened cement may be broken into a suitable size of granule form. This drug containing cement is then dried and stored before use. For more convenient application, the cement can be prepared in the surgical site as paste first. During this stage, the pasted can be introduced into the bone defects or implantation site before it becomes hardening.

EXAMPLE 1

The pure tetracalcium phosphate prepared by solid state reaction was ground to 270 mesh. 2 g of the powder was mixed with 0.3 g of anhydrous citric acid. The mixed powder was then further mixed with 0.7 ml pure water to form a thick sticky paste. This prepared paste set within several minutes. Shortly after set, surface pH of the setting cement was tested with pH indicator paper. The surface pH was higher than 5. This hardened paste was then aged in pure water, and it did not show any sign of disintegration.

EXAMPLE 2

Pure hydroxyapatite ceramics was decomposed by high temperature treatment to form o-tricalcium phosphate and tetracalcium phosphate by the following reaction $$Ca_{10}(PO_4)_6(OH)_2 \rightarrow 2\ Ca_3(PO_4)_2 + Ca_4P_2O_9 + H_2O$$

2 g of the above decomposed product was then mixed with 0.3 g of anhydrous citric acid. The mixed powder was then mixed with less than 1 ml of water to form a sticky paste. This paste became hardened within several minutes and resisted disintegration in an aqueous environment. If the decomposition of hydroxyapatite is carried out under vacuum at lower temperature, the decomposed products would be $\beta$-tricalcium phosphate and tetracalcium phosphate. This decomposed product can also be used to replace tetracalcium phosphate as cementing powder.

EXAMPLE 3

In examples 1 and 2, the setting reagent used was pure citric acid. In order to reduce the acidity of the setting reagent, the acidic citrate salts such as $NaH_2$ Citrate, $Na_2H$Citrate, $KH_2$Citrate, $K_2H$Citrate and the corresponding acidic ammonium citrate salts can be used to replace citric acid as the setting reagent. For example, 2 g of pure tetracalcium phosphate was premixed 0.3 g $NaH_2$Citrate first. This premixed powder was then intermixed with enough water to form a homogeneous mixed paste. After several minutes, the paste hardened. In other cases, $Na_3\ PO_4$, $Na_2HPO_4$, $K_2\ HPO_4$, $Na_3$ Citrate, $K_3$ Citrate can be used together with citric acid as a setting reagent which has higher pH than pure citric acid.

EXAMPLE 4

In examples 1 to 3, the cementing calcium phosphate cementing powder was premixed with the required setting reagent. The mixed powder was then intermixed with pure water to form cement. For storage and sterilization purpose, the above setting reagents such as citric acid, acidic citrate salts or pH adjusting salts can be dissolved in pure water to form a aqueous setting solution. The calcium phosphate cementing powder was then mixed with the setting solution to form a paste. For example, 1.5 g of citric acid and 1.5 g of trisodium citrate was dissolved in 5 ml pure water first to form an aqueous setting solution. 2 g of fully decomposed hydroxyapatite which contains mainly $\alpha$-tricalcium phosphate and tetracalcium phosphate was then mixed with about 0.8 ml of the above solution to form a paste. After mixing, the paste becomes hardened within several minutes.

EXAMPLE 5

In examples 1 to 4, the used of pure tetracalcium phosphate or fully decomposed hydroxyapatite as cementing powder to form moldable cement has been demonstrated. In order to meet a specific bioresorption rate, certain types of fillers can also be incorporated into this cementing powder system. Suitable fillers are calcium carbonate, calcium fluoride, calcium sulfate dihydrate, calcium sulfate hemihydrate, calcium sulfate anhydrous, calcium citrate, dicalcium phosphate, tricalcium phosphate, octacalcium phosphate, calcium phosphate apatite, magnesium oxide, magnesium hydroxide or biocompatible insoluble calcium organic salts. The maximum amount of fillers which can be used depends strongly on the activity and particle size of the filler. With fine particle size of inert filler, about 50% to 60% of the total weight of the cement powder can be inert filler. For large particle sizes such as granule form of filler, the filler which can be incorporated is about 75% of the total weight of the calcium phosphate cementing powder. For special active filler such as $\alpha$-tricalcium phosphate which is also involved in the cementing reaction, the amount incorporated can be as high as 90%. For example, 1 g of citric acid and 1 g of trisodium citrate was dissolved in 5 ml pure water to form a setting solution. 1 g of tetracalcium phosphate powder and 1 g of calcium sulfate anhydrous powder was mixed first. The mixed powder was then mixed with about 0.7 ml of the above setting solution to form a paste. This paste hardened within 5 minutes.

I claim:

1. A cementitious paste for orthopaedic, dental and maxillofacial applications comprising:
    a cementing powder of tetracalcium phosphate;
    a setting reagent consisting essentially of an acidic citrate, wherein the weight ratio of cementing powder to setting reagent lies between 2:1 and 15:1; and
    sufficient water to form said paste, and which paste, after setting has a pH greater than 5.

2. The paste of claim 1, wherein said cementing powder is fully decomposed hydroxyapatite which contains tetracalcium phosphate and $\alpha$-tricalcium phosphate.

3. The paste of claim 1, wherein said acidic citrate is selected from the group consisting of citric acid, $NaH_2$ citrate, $Na_2H$ citrate, $KH_2$citrate, $K_2H$ citrate, $(NH_4)_2H$ citrate and $NH_4H_2$ citrate salt.

4. The paste of claim 1, further comprising soluble pH adjusting reagents.

5. The paste of claim 4 wherein the soluble pH adjusting reagents are selected from the group consisting of $NaOH$, $KOH$, $NH_4OH$, $Na_3$ citrate, $K_3$ citrate, $(NH_4)_3$ citrate, $Na_3\ PO_4$, $Na_2HPO_4$, $K_3PO_4$ or $K_2HPO_4$.

6. The paste of claim 5 wherein the soluble pH adjusting reagents are premixed with said cementing powder and setting reagent.

7. The paste of claim 5 wherein the soluble pH adjusting reagents are dissolved in the water.

8. The paste of claim 1 further including up to approximately 85% by weight of an inert filler.

9. The paste of claim 8 wherein the inert filler is selected from the group consisting of $\alpha$-tricalcium phosphate, calcium phosphate, dicalcium phosphate, octacalcium phosphate, calcium carbonate, calcium sulfate dihydrate, calcium sulfate hemihydrate, calcium sulfate anhydrous, calcium oxide, calcium hydroxide, calcium fluoride, calcium citrate, magnesium oxide, and magnesium hydroxide.

10. The paste of claim 9 wherein the inert filler is of a particle size ranging from 1 micron to 20 mesh.

11. The paste of claim 1, wherein said water is saline.

12. The paste of claim 1 further including up to approximately 30% of an antibiotic.

13. The paste of claim 1 further including up to approximately 30% bone morphological protein.

14. The paste of claim 1 wherein the cementing powder contains partially decomposed hydroxyapatite which contains $\alpha$-tricalcium phosphate and tetracalcium phosphate as a major component and undecomposed hydroxyapatite as a minor component.

* * * * *